United States Patent [19]

Belykh et al.

[11] Patent Number: 4,875,479
[45] Date of Patent: Oct. 24, 1989

[54] SUTURAL MATERIAL

[75] Inventors: Sergei I. Belykh; Anatoly B. Davydov, both of Moscow; Anatoly D. Moschensky, Malakhovka; Nikolai N. Kanshin; Igor L. Kovalenko, both of Moscow; Jury B. Kirillov, Ryazan; Gennady I. Osipov; Rustam I. Utyamyshev, both of Moscow, all of U.S.S.R.

[73] Assignee: Vsesojuzny Nauchno-Issledovatelsky I Ispytatelny Institut Meditsinskoi Tekhniki, Moscow, U.S.S.R.

[21] Appl. No.: 191,149
[22] PCT Filed: Jul. 4, 1986
[86] PCT No.: PCT/SU86/00072
§ 371 Date: Feb. 19, 1988
§ 102(e) Date: Feb. 19, 1988
[87] PCT Pub. No.: WO88/00062
PCT Pub. Date: Jan. 14, 1988
[51] Int. Cl.⁴ .............................................. F24C 15/16
[52] U.S. Cl. .................................. 128/335.5; 525/205; 525/421; 525/937; 424/426; 424/428
[58] Field of Search ...................... 128/335.5; 525/205, 525/421, 937; 424/426, 428

[56] References Cited

U.S. PATENT DOCUMENTS

| | | | |
|---|---|---|---|
| 3,896,813 | 7/1975 | Kurtz | 128/335.5 |
| 3,938,515 | 2/1976 | Leeper et al. | 424/432 |
| 3,987,797 | 10/1976 | Stephenson | 128/335.5 |
| 4,036,227 | 7/1977 | Zaffaroni et al. | 424/428 |
| 4,136,250 | 1/1979 | Mueller et al. | 525/474 |
| 4,192,827 | 3/1980 | Mueller et al. | 525/123 |
| 4,275,183 | 6/1981 | Kuzma | 526/307.5 |
| 4,277,582 | 7/1981 | Mueller et al. | 525/421 |
| 4,300,820 | 11/1981 | Shah | 525/205 X |
| 4,582,052 | 4/1986 | Dunn et al. | 128/839 |

Primary Examiner—Richard J. Apley
Assistant Examiner—N. Paul
Attorney, Agent, or Firm—Burgess, Ryan & Wayne

[57] ABSTRACT

The sutural material consists of a base from a bio-resolvable polymer and a layer of a copolymer of N-vinylpyrrolidone with an alkylacrylate and/or an alkylmethacrylate deposited onto the base and containing an antimicrobal preparation or a mixture of preparations and having the period of its biodestruction shorter than that of the base, the thickness of this layer being equal to 0.1 to 1.0 of the base thickness.

2 Claims, No Drawings

SUTURAL MATERIAL

FIELD OF THE INVENTION

The present invention relates to the art of medical engineering and, more particularly, to a suture material.

PRIOR ART

Known in the art are non-resorbing suture material possessing antimicrobal activity, e.g. those based on polyethylene terephthalate or polypropylene with an antimicrobal preparation geomycin fixed thereon by means of a chemical bond. These suture materials ensure retention of soft tissues and the antimicrobal effect for two days (A. A. Shalimov et al., Polymers in Medicine, 1977, vol. VII, No. 1, pp. 19-26). However, threads from such a suture material are not biodegradable and the duration of their antimicrobal effect is rather limited.

Known in the art are suture materials based on a bioresorbing polymer, e.g. hydroxycellulose fibres containing sulphanylamide preparations attached to the base by means of covalent bonds. As the sulphanylamide preparations this material contains, for example, 2-(para-aminobenzosulphamido)-5-ethyl-1,3,4-thiadiazole or O-3-amino-3-desoxy-α-D-glucopyranosyl-(1→6)-O-[6-amino-6-desoxy-α-D glucopyranozyl-(1→4)]2-desoxy-D-streptomycin (kanamycin) (USSR Inventor's Certificate No. 338525, Int. Cl. C 08 b 15/02 1968). Threads from this material can undergo biodestruction under the effect of the organism fluids and ensure the antimicrobal effect for 16 days. However, such threads do not posess a sufficient tenacity and the amount of antibacterial agents capable of chemically being attached to the main chain of the suture material is very limited. Furthermore, during the chemical addition the molecule of the antimicrobal preparation is subjected to the effect of chemical reagents which can cause its partial destruction, wherefore the antimicrobal effect is either diminished or fully disappears.

DISCLOSURE OF THE INVENTION

The present invention is directed to the provision, by way of modification of the base, of a suture material exhibiting a high tenacity, incorporating any kinds of antimicrobal preparations and ensuring a broad interval of duration of the antimicrobal effect.

This object is accomplished by that the suture material according to the present invention comprising a base of a bioresolvable polymer and an antimicrobal preparation, according to the present invention contains a layer of a copolymer of N-vinylpyrrolidone with an alkylacrylate and/or an alkylmethacrylate deposited onto the base and containing an antimicrobal preparation or a mixture of preparations. The copolymer layer being biodegradable in a shorter length of time than the base. The layer thickness being equal to 0.1 to 1.0 of the base thickness.

The suture material contains an antimicrobal preparation or a mixture of preparations preferably in an amount of 1 to 40% by weight of the applied layer. The suture material according to the present invention has a number of advantages as compared to the known material, namely:

the suture material according to the present invention has a tensile strength higher by 15-20% than that of the known material;

tenacity of the knot joint of the thread is 25-30% higher than that of the known material;

the material according to the present invention makes it possible to use any kind of antimicrobal preparations including such preparations sensitive to all effects as quinoxaline derivatives;

it enables adjustment of duration of the antimicrobal effect in the injury zone within a wide time interval (from 3 to 20 days).

BEST MODE FOR CARRYING OUT THE INVENTION

The suture material according to the present invention contains a layer of a copolymer of N-vinylpyrrolidone with an alkylacrylate and/or alkylmethacrylate deposited on the base and contains an antimicrobal preparation or a mixture of antimicrobal preparations.

As the antimicrobal preparations useful in the present invention can be any preparation such as antibiotics, sulphanylamide preparations, quinoxaline derivatives, nitrofuran derivatives, hydroxyquinoline derivatives and the like.

The layer deposited onto the base biodestructs in a shorter period of time than the base. The thickness of this layer is 0.1 to 1.0 of the base thickness.

At a layer thickness of less than 0.1 of the base thickness the procedure of its application becomes substantially complicated, mechanical characteristics of the coating are impaired, while the amount of the antimicrobal preparation becomes so small that it does not provide sufficient antimicrobal effect. At a thickness above 1.0 of the base thickness strength characteristics of the suture material are also impaired thus resulting in the detachment of the deposited layer from the base during storage, the thread rigidity considerably increases and smoothness of the surface is impaired.

In the use of the suture material after application of a surgical suture under the influence of the fluids of the organism the antimicrobal preparation diffuses through the film of the copolymer deposited onto the base, the time of its liberation into the surrounding tissues depends on the copolymer film thickness. The total amount of the antimicrobal preparation can be predetermined within a broad range in advance at the stage of preparation of a composition for application onto the base and the deposited layer containing the antimicrobal preparation does not lower the physico-mechanical properties of the suture material. Owing to the fact that the copolymer containing the antimicrobal preparation biodegrades quicker than the base, the tenacity of the suture is retained at the required level during the entire period of the release of the antimicrobal preparation.

The suture material according to the present invention has been tested both "in vitro" and "in vivo".

During the study of properties of threads coated with a film of a copolymer of N-vinylpyrrolidone with alkylmethacrylates it has been found that the deposition of a polymer with an antibiotic onto an acid-treated Kapron thread results in an increase in breaking tenacity of thread No. 1 (93.5 tex) from 5.7 to 6.1 kg, while the knot tenacity is increased from 3.6 to 4.4 kg.

Similar results have been obtained for a dry thread as well. In this case the breaking tenacity of the thread both prior to and after application of a polymeric coating is 4.3 and 5.1 kg respectively, while the knot tenacity is equal to 2.2 and 3.2 kg respectively.

The suture material according to the present invention was subjected to clinical tests in the following embodiments: (1) a suture material based on an acid-treated Kapron coated with a copolymer of N-vinylpyrrolidone with butylmethacrylate containing 22% by weight of 1.4-di-N-oxide-2,3-bis(hidroxymethyl)-quinoxaline at the thickness of the deposited layer equal to 0.24 of the base thickness which corresponds to 6% by weight of the content of the antimicrobal preparation in the thread; (2) a suture material based on an acid-treated Kapron coated with a similar copolymer containing 10% by weight of 1.4-di-N-oxide-2,3-bis-(hydroxymethyl)-quinoxaline and 21% by weight of 1.4-di-N-oxide-2.3-bis-(acetoxymethyl)-quinoxaline at the thickness of the deposited layer equal to 0.23 of the base thickness which corresponds to the content of 1.9% by weight of the first antimicrobal preparation and 3.9% by weight of the second antimicrobal preparation in the thread; (3) a suture material based on an acid-treated Kapron coated with a similar copolymer containing 32% by weight of gentamycin sulphate at the thickness of the deposited layer equal to 0.14 of the base thickness which corresponds to the content of 4.5% of the antimicrobal preparation in the thread. This suture material was used for the formation of anastomoses on the gastro-intestinal tract in 29 patients, acute appendicitis—in 17 patients, peptic ulcer disease of the stomach—in 26 patients, calculous cholecystitis—in 19 patients, stomach carcinoma—in 11 patients and varix of limbs—in 22 patients. In all cases a reliable fixation of tissues was observed along with a full absence of purulent complications of the post-operation wounds and intestinal anastomoses.

The suture material according to the present invention in combination with connection members for the inner organs was tested in pediatric surgical practice in operations on parenchymatous organs in 27 patients (suturation of tissues of the intestine, liver) and in 17 patients in carrying out organ-retaining operations (spleen). No complications connected with the post-operational non-tightness of the sutures or purulent complications were observed. The blood and urine characteristics were normal.

Subjected to the tests was the suture material according to the present invention based on an acid-treated Kapron coated with a copolymer of N-vinylpyrrolidone with butylmethacrylate containing 6% by weight of 1.4-di-N-oxide-2.3-bis-(hydroxymethyl)-quinoxaline for suturation of the longitudinal sawing of the breast bone after operations on the heart. Instead of usually employed steel wire, 5–6 Z-like sutures were applied onto the breast bone. The wound healing and accretion of the breast bone occurred during usual time periods. No complications connected with suppuration of the sutures was observed. A full absence of pain feelings in motion usually observed in the case of using wire ligatures was noticed. A repeated operation for the removal of wire ligatures was excluded.

The suture material according to the present invention was also tested in plasty in the region of the soft and hard palates. Specific features of this operation reside in that owing to its specificity in this case there are always longer periods of healing (12–18 days) and adhesion is effected under conditions of permanent infectioning and influence of liquid media of the mouth cavity. Observations on 24 patients have shown that in all cases the wounds were healed by the primary adhesion without any complications.

The suture material according to the present invention was used for gnathic osteosynthesis in 35 patients in cases where no essential displacement of framgnets was observed. The tenacity characteristics of the suture material were quite adequate, while the presence of the antimicrobal coating made it possible to successfully use this method in 11 cases of open fractures.

For a better understanding of the present invention some specific examples illustrating the suture material as claimed are given hereinbelow.

EXAMPLE 1

A suture material comprising a base—Kapron thread of 93.5 tex thickness and a layer of a copolymer of butylmethacrylate with N-vinylpyrrolidone deposited onto the base and containing 6% by weight of the thread of 1.4-di-N-oxide-2.3-bis-(hydroxymethyl)-quinoxaline. The thickness of the deposited layer is equal to 0.24 of the base thickness. This material is produced by way of application, onto the above-mentioned Kapron thread, of a solution of the copolymer of butylmethacrylate with N-vinylpyrrolidone in ethanol (15 g of the copolymer in 100 ml of ethanol) containing 42 g of 1.4-di-N-oxide-2.3-bis-(hydroxymethyl)-quinoxaline (22% by weight of the copolymer). The thread is dried. The resulting suture material is subjected to testing. The test results are given in the Table hereinbelow.

EXAMPLE 2

A suture material consisting of a base—a thread of polyvinyl alcohol of 48 tex thickness and a layer, deposited onto the base, of a copolymer of hexylacrylate with N-vinylpyrrolidone containing 2% by weight of the thread of kanamycin (19% by weight of the copolymer). The thickness of the deposited layer is equal to 0.1 of the base thickness. This suture material is produced in a manner similar to that described in the foregoing Example 1 at the weight ratio of the copolymer, preparation and the solvent of 10:2.1:80 respectively. The results of tests of this material are shown in the Table hereinbelow.

EXAMPLE 3

A suture material comprising a base—a thread from monocarboxycellulose of 50.6 tex thickness and a layer of a copolymer of N-vinylpyrrolidone with methylmethacrylate and a copolymer of N-vinylpyrrolidone with ethylacrylate taken in the ratio of 1:1 deposited onto the base and containing 0.1% by weight of the thread of gentamycin sulphate and 0.40% by weight of the thread of 4-(para-aminobenzosulphamido)-6-methoxypyrimidine (1% by weight of the copolymer). The thickness of the deposited layer is equal to the base diameter. The material is produced in a manner similar to that described in Example 1 hereinbefore at the weight ratio between the copolymer, the mixture of preparations and the solvent of 100:0.5:95 respectively. The results of tests of this suture material are shown in the Table hereinbelow.

EXAMPLE 4

A suture material consisting of a base—a Kapron thread of 93.5 tex thickness and a layer of copolymer of N-vinylpyrrolidone and butylmethacrylate deposited onto the base and containing 3.12% by weight of the thread of 1.4-di-N-oxide-2.3-bis-(hydroxymethyl)-quinoxaline and 4.22% by weight of the thread of 1.4-di-N-oxide-2.3-bis-(acetoxymethyl)-quinoxaline (40% by weight of the copolymer). The thickness of the deposited layer is equal to 0.12 of the base thickness. The material is produced in a manner similar to that of Example 1 at the weight ratio of the copolymer, the mixture of the preparations and the solvent equal to 10.5:7:112 respectively. The results of tests are shown in the Table hereinbelow.

EXAMPLE 5

A suture material comprising a base—a Kapron thread of 93.5 tex thickness and a layer of the copolymer similar to that described in Example 1 hereinbefore, deposited onto the base and containing 4.5% by weight of the thread of gentamycin sulphate (25% by weight of the copolymer). The thickness of the deposited layer is equal to 0.11 of the base thickness.

The material is produced in a manner similar to that described in Example 1 at the weight ratio of the copolymer, the preparation and the solvent equal to 13.5:4.5:100 respectively. The results of tests of this suture material are shown in the following Table.

INDUSTRIAL APPLICABILITY

The suture material according to the present invention is intended for fixation of soft tissues in any kinds of surgical interventions and, first of all, under conditions of a possible infectioning of the ambient tissues.

TABLE

Comparative properties of the suturel material according to the present invention and of the known suturel materials

| No. | Types of thread | Initial characteristics Breaking tenacity, gf/tex | Knot tenacity, gf/tex | Characteristics after 10 days of residence in soft tissues Breaking tenacity, gf/tex | Knot tenacity, gf/tex | Maximum duration of the preparation detection in blood, days | Ratio of the period of biodestruction of the deposited layer and the base |
|---|---|---|---|---|---|---|---|
| 1 | 2 | 3 | 4 | 5 | 6 | 7 | 8 |
| 1 | The suturel material of this invention, Example 1 | 69 | 58 | 62 | 45 | 10 | 0.3–0.4 |
| 2 | The suturel material of this invention, Example 2 | 78 | 75 | 52 | 42 | 7 | 0.7–0.8 |
| 3 | The suturel material of this invention, Example 3 | 32 | 25 | 11 | 7 | 12–14 | 0.7–0.8 |
| 4 | The suturel material of this invention, Example 4 | 73 | 59.5 | 63 | 46 | 18–20 | 0.3–0.4 |
| 5 | The suturel material of this invention, Example 5 | 70 | 60 | 62 | 45 | 10 | 0.3–0.4 |
| 6 | Known suturel material based on hydroxycellulose fibers containing kanamycin | 18 | 15 | 6 | 2 | 10 | — |
| 7 | Known suturel material - Kapron thread | 63 | 40 | 60 | 38 | — | — |

We claim:

1. A suture material comprising a base thread of a bioresolvable polymer having deposited thereon a coating comprising a mixture of at least one antimicrobal preparation and a copolymer of N-vinylpyrrolidone with at least one composition selected from the group consisting of alkylacrylate and alkylmethacrylate the coating having a period of biodestruction shorter than the period of biodestruction of the base, and wherein the thickness of coating being equal to 0.1 to 1.0 of the base thread thickness.

2. A suture material of claim 1, wherein the suture material contains at least one antimicrobal preparation in an amount of from 1 to 40% by weight relative to the weight of the deposited coating.

* * * * *